(12) United States Patent
Steinbauer et al.

(10) Patent No.: US 8,642,312 B2
(45) Date of Patent: Feb. 4, 2014

(54) POLYPEPTIDE HAVING ESTERASE ACTIVITY AND RECOMBINANT ESTERASE AND USE THEREOF

(75) Inventors: Gerhard Steinbauer, Enns (AT); Micheal Stanek, Linz (AT); Peter Pojarliev, Vienna (AT); Wolfgang Skranc, Vienna (AT); Helmut Schwab, Graz (AT); Joannes Kierkels, Sittard (NL); Marcel Wubbolts, Sittard (NL); Harald Pichler, Deutschlandsberg (AT); Manuela Hermann, Werndorf (AT); Christoph Zenzmaier, Innsbruck (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 0 days.

(21) Appl. No.: 13/417,734

(22) Filed: Mar. 12, 2012

(65) Prior Publication Data

US 2012/0220014 A1 Aug. 30, 2012

Related U.S. Application Data

(62) Division of application No. 12/159,547, filed as application No. PCT/EP2006/011832 on Dec. 8, 2006, now Pat. No. 8,158,393.

(30) Foreign Application Priority Data

Dec. 27, 2005 (AT) ................. A 2081/2005

(51) Int. Cl.
*C12N 9/18* (2006.01)

(52) U.S. Cl.
USPC .......................................... 435/196

(58) Field of Classification Search
None
See application file for complete search history.

(56) References Cited

PUBLICATIONS

Lange et al., "Cloning Functional Expression, and Characterization of Recombinant Pig Liver Esterase" Chembiochem: A European Journal of Chemical Biology, vol. 2, No. 7, pp. 576-582 (Aug. 2, 2001).
Laetitia et al., "Purification and Molecular Cloning of Porcine Intestinal Glycerol-Ester Hydrolase: Evidence for its Identity with Carboxylesterase" European Journal of Biochemistry, vol. 257, No. 1, pp. 142-148, (Oct. 1, 1998).
Toone et al, "Enzymes in Organic Synthesis 49. Resolutions of Racemic Monocyclic Esters with Pig Liver Esterase" Tetrahedron Asymmetry, vol. 2, No. 3, pp. 207-222 (1991).
International Search Report for PCT/EP2006/011832, mailed Jun. 12, 2007.

*Primary Examiner* — Tekchand Saidha
*Assistant Examiner* — MD. Younus Meah
(74) *Attorney, Agent, or Firm* — Nixon & Vanderhye P.C.

(57) ABSTRACT

Polypeptide and recombinant protein having esterase activity which exhibit the amino acid sequence SEQ. ID. No. 1 and the use thereof.

3 Claims, 5 Drawing Sheets

Stereoselective esterase activity on methyl 5-Chloro-2-(1-methylethyl)-4-pentenoate A: Activity on the racemic substrate: *P. pastoris* X-33 transformants pGAPZ A PLE-ER    pGAPZ A PLE+ER
pGAPZ A APLE-ER   pGAPZ A APLE+ER B: Activity on the racemic substrate vs. (S) enantiomer pGAPZ A APLE-ER (S) enantiomer                          racemate pGAPZ A PLE-ER

SDS-PAGE of recombinant APLE

1: Page Ruler Protein Ladder (Fermentas)
2: Commercially available PLE
3: *P. pastoris* X-33 with integrated pGAPZ A (control strain)
4: *P. pastoris* X-33 with integrated pGAPZ A APLE-ER

Figure 3

Induced expression of pig liver esterases with the AOX1 promoter

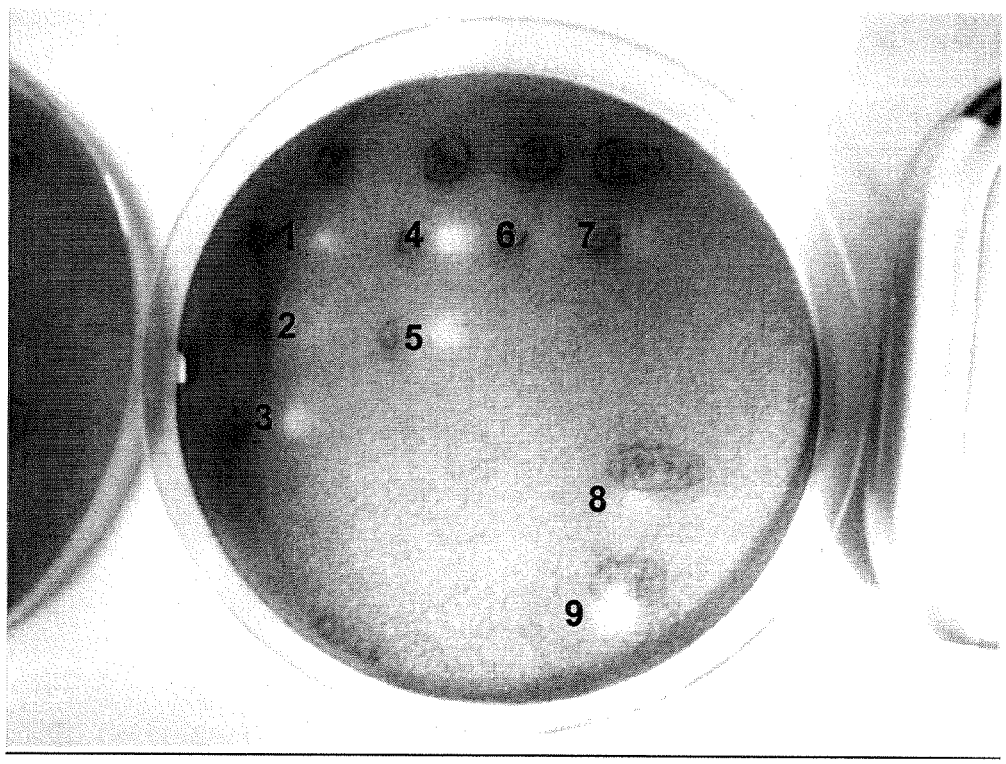

1: *P. pastoris* KM71 with integrated pPIC9 APLE-ER
2: *P.* pastoris KM71 with integrated pPIC9 APLE-ER
3: P. pastoris KM71 with integrated pPIC9 APLE-ER
4: P. pastoris KM71 with integrated pPIC9 APLE+ER
5: P. pastoris KM71 with integrated pPIC9 APLE+ER
6: P. pastoris KM71 with integrated pPIC9 PLE-ER
7: P. pastoris KM71 with integrated pPIC9 PLE+ER
8: P. pastoris KM71
9: Commercially available PLE

Figure 4

SEQ ID No 1

Protein sequence of rAPLE

GQPASPPVVDTAQGRVLGKYVSLEGLAQPVAVFLGVPFAKPPLGSLRFAPPQPAEPWSFVKNTTSYPPMCCQEPI
GGQMLSDLFTNRKERLIPEFSEDCLYLNIYTPADLTKRGRLPVMVWIHGGGLVVGGASTYDGLALAAHENVVVVA
IQYRLGIWGFFSTGDEHSRGNWGHLDQVAALHWVQENIANFGGDPGSVTIFGESAGGESVSVLVLSPLAKNLFHR
AISESGVAFTAGLVRKDMKAAAKQIAVLAGCKTTTSAVFVHCLRQKSEDELLDLTLKMKFFALDLHGDPRESHPF
LTTVVDGVLLPKMPEEILAEKDFNTVPYIVGINKQEFGWLLPTMMGFPLSEGKLDQKTATSLLWKSYPIANIPEE
LTPVATDKYLGGTDDPVKKKDLFLDLMGDVVFGVPSVTVARQHRDAGAPTYMYEFQYRPSFSSDKKPKTVIGDHG
DEIFSVFGFPLLKGDAPEEEVSLSKTVMKFWANFARSGNPNGEGLPHWPMYDQEEGYLQIGVNTQAAKRLKGEEV
AFWNDLLSKEAAKKPPKIKHAEL

SEQ ID No 2:

Nucleotide sequence of rAPLE

```
gggcagccag cctcgccgcc tgttgtggac actgcccagg gccgagtcct ggggaagtac
gtcagcttag aaggcctggc acagccggtg gccgtcttcc tgggagtccc ttttgccaag
cccctctcg  gatccttgag gtttgctccg ccgcagcctg cagaaccatg gagcttcgtg
aagaacacca cctcctaccc tcccatgtgc tgccaagagc caattggggg acagatgctc
tcagatctat ttaccaacag aaaggagagg ctcattccgg agttttctga agactgtctc
tacctaaata tttacacccc tgctgacctg acaaagaggg gcagactgcc ggtgatggtg
tggatccacg gaggaggtct ggtggtgggc gggcttcca  cctatgatgg actgcccctc
gctgcgcatg aaaacgtggt ggtggtggcc atccagtacc gcctgggcat ctggggattc
ttcagcacag gggacgaaca cagccgggc  aactgggtc  acttggacca ggtggccgca
ctgcactggg tccaggagaa catcgccaac tttggaggcg acccaggctc tgtgaccatc
tttggagagt cagcaggagg ggaaagtgtc tctgttctgg tgttgtctcc cttggccaag
aacctcttcc accgggccat ctctgagagt ggcgtggcct tcactgctgg cctggtcagg
aaggacatga aggctgcagc taagcaaatt gctgtccttg ctgggtgtaa aaccaccacc
tcggctgtct tgttcactgc cctgcgccag aagtcggagg acgagctctt ggacttaacg
ctgaagatga aatttttcgc tcttgatttg catggagacc ccagagagag ccatcccttc
ctgaccactg tggtggatgg agtgctgctg cccaagatgc ctgaagagat tctggctgaa
aaggatttca acactgtccc ctacatcgtg ggaatcaaca agcaagagtt tggctggctt
ctgccaacga tgatgggctt ccccctctct gaaggcaagc tggaccagaa gacggccacg
tcactcctgt ggaagtccta ccccatcgct aacatccctg aggaactgac tccagtggcc
actgacaagt atttgggggg gacagacgac cccgtcaaaa agaaagacct gttcctggac
ttgatggggg atgtggtgtt tggtgtccca tctgtgacgg tggcccgtca acacagagat
gcaggagccc ccacctacat gtatgagttt cagtatcgcc caagcttctc atcggacaag
aaacccaaga cggtgatcgg ggaccacggg gatgagatct tctccgtctt tggttttcca
ctgttaaaag gcgatgcccc agaagaggag gtcagtctca gcaagacggt gatgaaattc
tgggccaact tgctcgcag  tgggaacccc aatggggagg gctgccca  ttggccgatg
tacgaccagg aagaaggta  ccttcagatc ggcgtcaaca cccaggcagc caagaggctg
aaaggtgaag aagtggcctt ctggaacgat ctcctgtcca aggaggcagc aaagaagcca
cccaagataa agcatgctga gctgtga
```

Figure 5

SEQ ID. No. 3: Primer 1
5'-CAGAATTCATGGCTATCGGGCAGCCAGCCTCGC-3'

SEQ ID No. 4: Primer 2
5'-CCGGAATTCAGCCTCCCCTTCACAGCTCAG -3'

SEQ ID No. 5: EcoRIalpha1
5'-TCTTCGAAGAATTCACGATGAGATTTCCTTCAATTTTTACTGC-3'

SEQ ID No. 6: alphaPLE2
5'-GAGGCTGGCTGCCCAGCTTCAGCCTCTCTTTTCTCG-3'

SEQ ID No. 7: PLEalpha1
5'-AGAGAGGCTGAAGCTGGGCAGCCAGCCTCGCCG-3'

SEQ ID No. 8: EcoRIPLE+ER2
5'-ATGGTACCGAATTCTCACAGCTCAGCATGCTTTATCTTG-3'

SEQ ID No. 9: EcoRIPLE2
5'-ATGGTACCGAATTCTCACTTTATCTTGGGTGGCTTCTTTG-3'

POLYPEPTIDE HAVING ESTERASE ACTIVITY AND RECOMBINANT ESTERASE AND USE THEREOF

CROSS REFERENCE TO RELATED APPLICATIONS

This application is a divisional of application Ser. No. 12/159,547 filed Nov. 3, 2008, now U.S. Pat. No. 8,158,393 which is a 371 of PCT/EP2006/011832 filed Dec. 8, 2006, which claims priority to Austrian Application No. A 2061/2005 filed Dec. 27, 2005, the entire contents of each of which are hereby incorporated by reference.

The invention relates to a novel polypeptide having esterase activity, especially having 2-alkyl-5-halopent-4-en-ecarboxylesterase activity, and to an enzymatically active recombinant protein having esterase activity and to the use thereof for resolving racemates of 2-alkyl-5-halopent-4-en-ecarboxylic ester enantiomer mixtures.

BACKGROUND OF THE INVENTION

Enantiomerically enriched 2-alkyl-5-halopent-4-enecarboxylic acids and their esters are valuable intermediates for preparing pharmaceuticals, such as, for instance, for delta-amino-gamma-hydroxy-omega-arylalkanecarboxamides, which have renin-inhibiting properties and can be used as antihypertensive agents in pharmaceutical preparations.

Esterases are generally employed in the resolution of racemates and asymmetrization.

However, only very few esterases suitable for preparing chiral compounds are commercially available.

The use of esterase extracts from pig liver is known on the preparative scale. Pig liver esterase (PLE) was isolated long ago from natural sources, and its activity has also been known for a long time (Simonds, J. P. (1919) Amer. J. Physiol. 48, 141; Bamann, E. et al. (1934) Hoppe-Seyler Z. 229, 15; Falconer J. S. and Taylor, D. B. (1946) Biochem. J. 40, 831-834).

Various studies have also already been carried out in order to characterize PLE (Heymann, E. and Junge, W. (1979) Eur. J. Biochem. 95, 509-518; Lehner, R. and Verger, T. (1997) Biochemistry 36, 1861-1868).

It has further been possible to show, for example in WO 01/09079, that esterase extracts from pig liver can selectively hydrolyze the (R) enantiomer of methyl 5-chloro-2-(1-methylethyl)-4-pentenoate.

However, the use of such esterase extracts from natural sources, such as pig liver, is associated with disadvantages. In the first place, the qualities of the different batches vary and thus make it difficult to optimize industrial processes. Secondly, the use of animal resources in the manufacture of pharmaceutical products is undesired because the presence of viruses and prions cannot always be precluded.

For these reasons there is a need to produce recombinant pig liver esterases of standardized quality in microorganisms.

The cloning of putative esterase genes is described for example in FEBS Lett. (1991), 293, 37-41. The first functional expression of an active pig liver esterase enzyme was described for the first time in WO 02/48322.

WO 2004/055177 describes the preparation of further recombinant esterases by site directed mutagenesis of the recombinant pig liver esterase of seq. ID No. 1 (rPLE) from WO 02/48322. As is evident from the description of WO 2004/055177 and from the article authored by the same inventors in Protein Engineering, 16, 1139-1145, 2003, the modifications of the rPLE sequence from WO 02/48322 were chosen so that a recombinant intestinal pig esterase (PICE) disclosed in David et al., (1998) Eur. J. Biochem. 257, 142-148, is obtained.

The resolution of racemic 2-alkyl-5-halopent-4-enecarboxylic esters is not described in any of these articles.

SUMMARY OF THE INVENTION

However, since the need for esterases which have the desired stereoselective activity for 2-alkyl-5-halopent-4-enecarboxylic esters and which can easily be prepared biotechnologically is not met, it was an object of the present invention to provide a corresponding novel recombinant esterase.

In an attempt to isolate and to clone the gene described in FEBS Lett. (1991), 293, 37-41 and WO 02/48322 for known pig liver esterase (PLE) as cDNA starting from mRNA from pig liver, a second, novel esterase sequence was found in addition to the known PLE sequence. Following expression of the two sequences, in which the corresponding proteins or esterases, namely the known rPLE and a novel, recombinant "alternative" esterase (rAPLE), was prepared, it unexpectedly emerged that only the rAPLE is capable of selective resolution of racemic 2-alkyl-5-halopent-4-enecarboxylic esters.

It was thus possible to achieve the object of the present invention by a novel polypeptide having esterase activity and a novel recombinant esterase (rAPLE), whose amino acid sequence differs in 21 of a total of 548 amino acids from the known PLE sequence.

The novel rAPLE differs in the amino acid sequence also from the known pig intestinal carboxylesterase (PICE) in 12 of a total of 548 amino acids. However, PICE is found in the pig intestinal tract.

The present invention accordingly relates to a polypeptide having esterase activity, which comprises the amino acid sequence SEQ. ID. No. 1.

The present invention further relates to a novel recombinant protein having esterase activity, which comprises the amino acid sequence SEQ. ID. No. 1.

The polypeptide and the recombinant rAPLE of the invention have the ability to resolve stereoselectively racemic 2-alkyl-5-halopent-4-enecarboxylic esters of the formula (I)

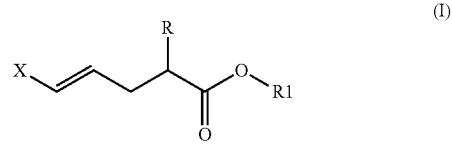

(I)

in which R is a $C_1$-$C_6$-alkyl radical, $R_1$ is $C_1$-$C_4$-alkyl and X is chlorine, bromine or iodine.

The polypeptide of the invention having esterase activity, and the novel recombinant esterase rAPLE differ, as stated above, in 21 of a total of 548 amino acids of the known sequence disclosed in FEBS Lett. (1991), 293, 37-41 and in 12 of a total of 548 amino acids from the known PICE protein disclosed in David et al., (1998) Eur. J. Biochem. 257, 142-148.

The sequence of the protein of the novel rAPLE of the invention differs in the following amino acid positions from the known sequence of the PLE protein:

| APLE | Position | PLE |
|------|----------|-----|
| Glu  | 73       | Asp |
| Ile  | 75       | Val |
| Gly  | 76       | Val |
| Gly  | 77       | Glu |
| Leu  | 80       | Thr |
| Arg  | 87       | Gly |
| Ile  | 92       | Thr |
| Pro  | 93       | Leu |
| Val  | 129      | Leu |
| Ser  | 133      | Pro |
| Thr  | 134      | Met |
| Leu  | 138      | Val |
| Ala  | 139      | Val |
| Phe  | 234      | Leu |
| Ala  | 236      | Val |
| Gly  | 237      | Ala |
| Phe  | 286      | Leu |
| Ala  | 287      | Thr |
| Leu  | 290      | Phe |
| Pro  | 294      | Gln |
| Thr  | 302      | Pro |

The protein of the invention and the novel recombinant rAPLE may moreover be in the form of a modified sequence as shown in SEQ ID No 1, which can be obtained for example by usual modifications such as, for instance, exchange, deletion or attachment of amino acid(s) in the sequence at the N or C terminus, such as, for instance, GluAlaGluAla from the α factor signal sequence, or by fusion to other proteins.

The invention also further includes muteins having modifications within the protein sequence of the enzyme of the invention having the appropriate activity, in particular on 2-alkyl-5-halopent-4-enecarboxylic esters. Muteins can be obtained for example by modifications of the DNA which codes for the enzyme of the invention, by known mutagenesis techniques (random mutagenesis, site-directed mutagenesis, directed evolution, gene shuffling etc.) so that the DNA codes for an enzyme which differs at least by one amino acid from the enzyme of the invention, and subsequent expression of the modified DNA in a suitable host cell. The invention thus also includes modified DNA sequences as shown in SEQ ID. No 1, obtained by the mutations, deletions, extensions, fusions described above, and which code for enzymes having the desired esterase activity.

Esterase activity, especially 2-alkyl-5-halopent-4-enecarboxylesterase activity, is defined in this connection as the ability to resolve racemates of 2-alkyl-5-halopent-4-enecarboxylic esters of the formula (I).

The polypeptide of the invention and the recombinant rAPLE can be prepared as described below:

Firstly, mRNA is isolated from pig liver using a suitable kit, and then the cDNA is generated by reverse transcription based on the mRNA extract.

Subsequently, specific PCR primers based on the sequence of the known pig liver esterase gene of GenBank accession No. X63323 (Matsushima et al., 1991) is prepared, followed by amplification and cloning.

These specific primers are:

```
Primer 1:
                                       (SEQ ID NO: 3)
5'-CAGAATTCATGGCTATCGGGCAGCCAGCCTCGC-3'

Primer 2:
                                       (SEQ ID NO: 4)
5'-CCGGAATTCAGCCTCCCCTTCACAGCTCAG-3'
```

This part of the primers which comprises the appropriate nucleotide sequences coding for the PLE protein and which is obligatorily present in the primers is in bold script.

The other sequence part of the primers comprises for example information for cleavage sites for restriction endonucleases (in italics) or sequence elements which are important for expression. This part may vary in the preparation of the rAPLE of the invention.

Amplification then takes place with primers 1 and 2 by prior art PCR methods.

The PCR product is subsequently used to prepare by prior art methods expression constructs for heterologous expression of the encoded rAPLE protein in suitable host organisms. This preferably entails the PCR product being initially cloned into suitable plasmid vectors.

The recombinant plasmids obtained in this way are then transformed into a suitable host, for example *Escherichia coli*. Inserts of several resulting clones are then sequenced.

Unexpectedly, 2 groups of recombinant clones with different sequences were identified therein, one being 100% identical to the expected sequence for PLE according to Matsushima et al., (1991) FEES Lett. 293, 37-41, and a novel nucleotide sequence as shown in SEQ. ID. No. 2 (APLE sequence) which leads after expression to the amino acid sequence SEQ. ID. No. 1 of the invention.

The present invention further relates to a nucleic acid or nucleotide sequence which codes for the polypeptide of the invention and the recombinant esterase rAPLE.

For example, such a nucleic acid has the nucleotide sequence shown in SEQ. ID. No. 2.

The invention also relates further to nucleotide sequences which include a nucleotide sequence which codes for the polypeptide of the invention and the recombinant esterase rAPLE, or comprises the nucleotide sequence shown in SEQ. ID. No. 2.

A further possibility is to prepare appropriate oligonucleotides corresponding to nucleic acid sequences according to the present invention which code for the esterase of the invention by standardized synthetic techniques, for example with use of automated DNA synthesizers.

The purely synthetic preparation of the nucleic acid sequences which code for the esterase of the invention is particularly advantageous for use in the production of pharmaceuticals or their intermediates, because enzymes are thus not obtained from animal sources.

Expression of the two sequences found (PLE and APLE sequences) then takes place.

The known pig liver esterase (PLE, Swiss-Prot ID Q29550) comprises an N-terminal signal sequence and a C-terminal ER retention signal, the last 4 amino acids HAEL.

In order to express the known PLE and the novel APLE, vectors in which the sequences are introduced into suitable expression systems constructed. These expression constructs are then transformed into suitable host cells.

Suitable host cells in this connection are for example microorganisms, animal cell lines and plants. Eukaryotic microorganisms are preferred, and fungi are particularly preferred. Examples thereof are *Saccharomyces cerevisiae, Pichia pastoris, Kluyveromyces lactis* or *Aspergillus* sp.

Expression may be secretory or intracellular and both inducible and constitutive.

The proteins are preferably expressed in a secretory manner, in which case vectors in which the sequences of PLE and APLE are linked N-terminally to the α factor signal sequence of *S. cerevisiae* are preferably constructed.

It is further possible to prepare constructs in which the C-terminal tetrapeptide HAEL, which serves as ER retention signal as described for example in Hardwick et al., (1990) EMBO J. 9, 623-630, is additionally deleted.

A further preferred expression is inducible expression of constructs with or without ER retention signal.

Unexpectedly, constructs having the ER retention signal can also be expressed and lead to an rAPLE which is capable of selective resolution of racemic 2-alkyl-5-halopent-4-enecarboxylic esters.

The amino acid sequence of the novel esterase rAPLE which is derived from the nucleotide sequence of the APLE gene is depicted in SEQ ID No. 1.

It has unexpectedly been possible to find that the novel polypeptide or the rAPLE protein is able, in contrast to the known rPLE, in each case obtained by expression of the DNA segments coding for APLE and PLE, respectively, for example in *P. pastoris* cells, to resolve racemic 2-alkyl-5-halopent-4-enecarboxylic esters stereoselectively.

The invention accordingly further relates to the use of the polypeptide having esterase activity and of the recombinant esterase (rAPLE) of the invention, which have at least 80% identity to the sequence shown in SEQ ID No. 1, for resolving racemates of 2-alkyl-5-halopent-4-enecarboxylic esters of the formula (I)

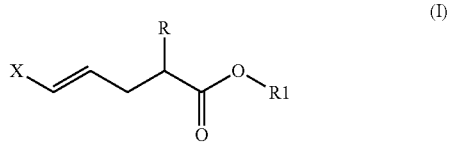

(I)

in which R is a $C_1$-$C_6$-alkyl radical, $R_1$ is $C_1$-$C_4$-alkyl and X is chlorine, bromine or iodine.

The polypeptide having esterase activity and the recombinant esterase (rAPLE) of the invention preferably have at least 90%, particularly preferably at least 98%, identity to the sequence of the protein shown in SEQ ID No. 1. It is also possible to employ polypeptide having an esterase activity or the recombinant esterase (rAPLE) of the invention with modified DNA sequences shown in SEQ ID. No. 1, obtained by usual modifications such as, for instance, mutations, deletions, extensions, fusions, which code for enzymes having the desired esterase activity.

In this connection, enantiomerically enriched 2-alkyl-5-halopent-4-enecarboxylic acids or their esters of the formula (II)

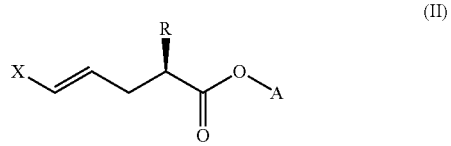

(II)

in which R is a $C_1$-$C_6$-alkyl radical, A is equal to H, $R_1$, where $R_1$ may be $C_1$-$C_4$-alkyl, or $R_2$, where $R_2$ is an alkyl group, but is not equal to $R_1$, and X is chlorine, bromine or iodine, are obtained by an enantiomeric mixture of a 2-alkyl-5-halopent-4-enecarboxylic ester of the formula (I)

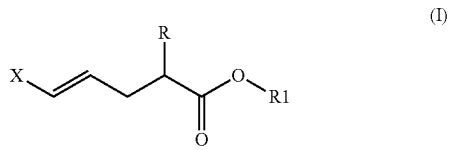

(I)

in which R, $R_1$ and X are as defined above, being converted by means of the polypeptide of the invention or of the rAPLE of the invention in the presence of water or an alcohol of the formula $R_2OH$, where $R_2$ is an alkyl group which is not equal to $R_1$, as nucleophile, and a) either the remaining enantiomerically enriched 2-alkyl-5-halopent-4-enecarboxylic ester of the formula (II) with A equal to $R_1$ being isolated or b) if an alcohol is employed as nucleophile, the resulting enantiomerically enriched 2-alkyl-5-halopent-4-enecarboxylic ester of the formula (II) with A equal to $R_2$ being isolated, or c) if water is employed as nucleophile, the resulting 2-alkyl-5-halopent-4-enecarboxylic acid of the formula (II) with A equal to H being isolated.

R in the formula (II) is a $C_1$-$C_6$-alkyl radical such as, for instance, methyl, ethyl, n- and i-propyl, n-, i- and t-butyl, pentyl and hexyl.

$C_1$-$C_4$-Alkyl radicals are preferred, and the i-propyl radical is particularly preferred.

A is H, $R_1$, where $R_1$ is a $C_1$-$C_4$-alkyl radical, preferably a $C_1$-$C_2$-alkyl radical and particularly preferably a methyl radical, or $R_2$, where $R_2$ is an alkyl radical which is not equal to $R_1$. $R_2$ is particularly preferably a $C_1$-$C_6$-alkyl radical.

X is chlorine, bromine or iodine, preferably chlorine.

Enantiomerically enriched compounds mean in this connection those which exhibit an enantiomeric excess (ee) of >80%, preferably of >90% and particularly preferably of >97%.

The enzyme of the invention can moreover be used in any form. For example as dispersion, as solution, immobilized, as crude enzyme, as enzyme which has been obtained from its source by a combination of known purification methods, as whole cells (where appropriate immobilized and/or permeabilized) which have the required enzymatic activity (naturally or through genetic modifications) or in a lysate of such cells.

The reaction temperature for the conversion of the invention is normally between 0 and 90° C., preferably between 10 and 60° C. The pH of the reaction solution is between 4 and 11, preferably between 6 and 9.

The choice of the solvent depends on the nucleophile employed.

If, for example, water is the nucleophile, solvents which can be employed are water, a mixture of water with a water-miscible solvent, for example with an alcohol such as, for instance, methanol, ethanol, isopropanol, t-butanol, etc., dioxane, tetrahydrofuran, acetone or dimethyl sulfoxide or a two-phase system of water and of a water-immiscible solvent, for example an aromatic compound such as, for instance, toluene, xylene, etc., an alkane such as, for instance, hexane, heptane, cyclohexane, etc., ether such as, for instance, diisopropyl ether, methyl t-butyl ether, etc. If the nucleophile is an alcohol, the solvent preferably employed is the alcohol $R_2OH$ where $R_2$ is an alkyl group which is not, however, equal to $R_1$. However, it is also possible to use mixtures of the alcohol with an organic solvent such as, for instance, tetrahydrofuran, heptane, toluene, hexane, $CH_3CN$, methyl t-butyl ether etc.

After the enzymatically catalyzed racemate resolution has taken place, the desired final product is isolated. This may be either the remaining enantiomerically enriched 2-alkyl-5-halopent-4-enecarboxylic ester of the formula (II) with A equal to $R_1$, or if water is the nucleophile the enantiomerically enriched 2-alkyl-5-halopent-4-enecarboxylic acid of the formula (II) with A equal to H which has formed, or if the alcohol is the nucleophile the enantiomerically enriched 2-alkyl-5-halopent-4-enecarboxylic ester of the formula (II) with A equal to $R_2$.

The isolation can take place for example by conventional methods such as, for instance, extraction, crystallization, column chromatography, distillation, etc.

The method of the invention results in the corresponding acids or esters of the formula (I) in theoretical yields of up to 98% yield and with an e.e. of up to >99%.

BRIEF DESCRIPTION OF THE DRAWINGS

The invention will now be described in more detail with reference to the accompanying drawings, in which:

FIG. 3 depicts Induced expression of pig liver esterases with the AOX1 promoter.

FIG. 4 shows SEQ ID NO 1: Protein sequence of rAPLE, and SEQ ID NO 2: Nucleotide sequence of rAPLE; and FIG. 5 shows SEQ ID NO 3: Primer 1,
SEQ ID NO: 4: Primer 2,
SEQ ID NO: 5: EcoRIalpha1,
SEQ ID NO: 6: alphaPLE2,
SEQ ID NO: 7: PLEalpha1,
SEQ ID NO: 8: EcoRIPLE+ER2,
SEQ ID NO: 9: EcoRIPLE2.

Figure 1:
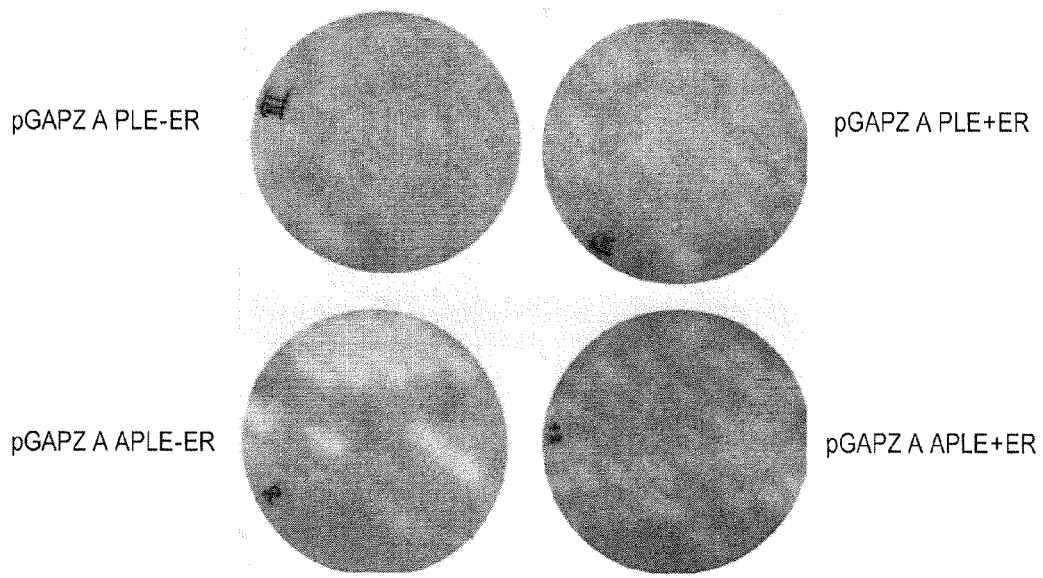
FIG. 1 depicts Stereoselective esterase activity on methyl 5-chloro-2-(1-methylethyl)-4-pentenoate.
Figure 1:
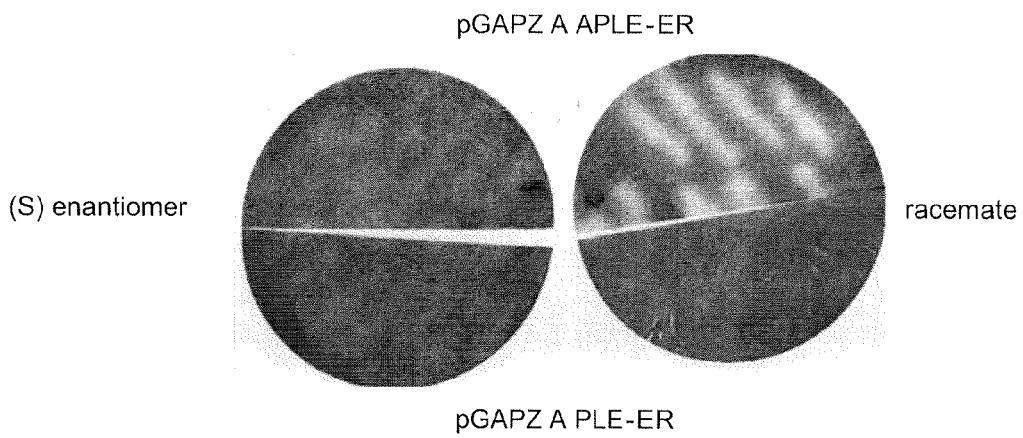

EXAMPLE 1 mRNA Isolation and Generation of cDNA 0.7 g of liver from a freshly slaughtered pig, obtained from a local abattoir, was frozen in liquid nitrogen and homogenized with a mortar, and the liberated mRNA was isolated or extracted using the Fast Track mRNA extraction kit 2.0 (Invitrogen, Carlsbad, Calif., USA) in accordance with the statements made by the manufacturer (Fast Track 2.0 kit manual; version J; 082301; 25-0099). The extraction afforded a total amount of 12.9 µg of mRNA.

0.26 µg of this mRNA was then used as template for generating cDNA using the SuperScript III First-Strand synthesis system for RT-PCR according to the manufacturer's statements.

EXAMPLE 2

Amplification and Cloning of cDNA Fragments from Pig Liver

Specific primers based on the sequence of the pig liver esterase gene of GenBank accession No. X63323 (Matsushima et al., 1991) were prepared:

```
Primer 1:
                                        (SEQ ID. No. 3)
5'-CAGAATTCATGGCTATCGGGCAGCCAGCCTCGC-3'

Primer 2:
                                        (SEQ ID No. 4)
5'-CCGGAATTCAGCCTCCCCTTCACAGCTCAG-3'
```

Bases homologous to the known PLE sequence are in bold script. Recognition sequences for restriction endonucleases are italicized for emphasis.

The amplification took place in a 50 µl mixture with 1 U of Phusion DNA polymerase (Finnzymes, Espoo, Finland), with 500 ng of cDNA as template, 20 µmol each of primer 1 and 2, 5 µl of a dNTP mix (2 mM each), all in 1× Phusion HF buffer in accordance with 'Phusion High-Fidelity DNA Polymerase' manual (Finnzymes), starting with a 30 second denaturation step at 98° C., followed by 30 cycles (10 sec 98° C., 20 sec 68° C., 1 min 72° C.) for amplification and a final incubation at 70° C. for 8 min to prepare complete products.

This PCR resulted in a DNA fragment with a size of 1.8 kb (found by agarose gel electrophoresis).

This PCR product was then purified using the Qiaquick kit (Qiagen, Hilden, Germany) in accordance with the manual included.

About 0.1 µg of the purified PCR product was cut with the restriction endonuclease EcoRI and cloned into the plasmid vectors pHILZ and pHIL-D2 via the EcoRI cleavage sites.

The vectors were then transformed into TOP10 electrocompetent cells prepared in accordance with 'Current Protocols in Molecular Biology'.

Inserts of several resulting clones were sequenced using the 'Dye Deoxy Terminator Cycle Sequencing' kit (Applied Biosystems Inc., Forster City, Calif., USA).

Two sequences were identified thereby, one corresponding 100% to the expected sequence published by Matsushima et al., (1991) FEBS Lett. 293, 37-41, and the other sequence corresponding to SEQ ID No. 2.

EXAMPLE 3

Introduction of the α Factor Signal Sequence and Variations of the C-Terminal End In order to enable secretory expression of the known protein PLE and the protein rAPLE of the invention, vectors in which the sequence of PLE and APLE was connected N-terminally to the α factor start sequence of the cloning vector pPICZ α (Invitrogen) were constructed. In addition, constructs in which the C-terminal tetrapeptide HAEL was deleted were prepared.

PCR I: The EcoRIalpha1/alphaPLE2 primer pair was used to amplify the α factor signal sequence of the cloning vector pPICZ α (Invitrogen). The PCR was carried out in a 50 µl mixture (2 ng of template, 0.5 µM of each primer, 0.2 mM dNTPs, 1 U of the Phusion DNA polymerase (Finnzymes) all in 1× Phusion HF buffer in accordance with the 'Phusion High-Fidelity DNA Polymerase' manual (Finnzymes)).

Denaturation at 95° C. for 3 minutes was followed by amplification in 30 cycles (30 sec 95° C., 30 sec 57° C., 15 sec 72° C.) and a final step at 72° C. for 7 min.

PCR II: The PLE and APLE sequences were amplified from pHILZ plasmids using either the PLEalpha1/EcoRIPLE+ER2 primer pair or the PLEalpha1/EcoRIPLE2 (deletion of the C-terminal HAEL tetrapeptide) primer pair.

These PCRs were again carried out in 50 µl mixtures (2 ng of template, 0.5 µM of each primer, 0.2 mM dNTPs, 1 U of the Phusion DNA polymerase (Finnzymes) all in 1× Phusion HF buffer in accordance with the 'Phusion High-Fidelity DNA Polymerase' Manual (Finnzymes)).

A denaturation at 95° C. for 3 minutes was followed by amplification in 30 cycles (30 sec 95° C., 30 sec 57° C., 15 sec 72° C.) and a final step at 72° C. for 7 min.

PCR III: 3 µl of the products from PCR I and PCR II were used to combine these two products by primerless PCR.

The extension was carried out in a 45 µl mixture with 0.2 mM dNTPs, 1 U of the Phusion DNA polymerase (Finnzymes) all in 1× Phusion HF buffer.

The reaction mixture was heated at 95° C. for 3 minutes and then 10 cycles with 30 sec at 95° C. and 45 sec at 72° C. were carried out. To amplify these overlapping extension products, 5 µl of primer mix (3 µl of water, 1 µl of 5 µM EcoRIalpha1 primer and 1 µl of 5 µM EcoRIPLE+ER2 or EcoRIPLE2 primer) were added. The products were amplified with 20 PCR cycles (30 sec 95° C., 30 sec 57° C., 1 min 72° C.) and a single temperature stop at 72° C. for 7 min.

```
Primer sequences:
EcoRIalpha1:
                                       (SEQ ID No. 5)
5'-TCTTCGAAGAATTCACGATGAGATTTCCTTCAATTTTTACTGC-3' alphaPLE2:
                                       (SEQ ID No. 6)
5'-GAGGCTGGCTGCCCAGCTTCAGCCTCTCTTTTCTCG-3'

PLEalpha1:
                                       (SEQ ID No. 7)
5'-AGAGAGGCTGAAGCTGGGCAGCCAGCCTCGCCG-3'

EcoRIPLE + ER2:
                                       (SEQ ID No. 8)
5'-ATGGTACCGAATTCTCACAGCTCAGCATGCTTTATCTTG-3'

EcoRIPLE2:
                                       (SEQ ID No. 9)
5'-ATGGTACCGAATTCTCACTTTATCTTGGGTGGCTTCTTTG-3'
```

Regions with homology to the templates in bold, recognition sequences for restriction endonucleases in italics.

EXAMPLE 4

Construction of Expression Constructs for the Heterologous Expression of Pig Liver Esterases in *Pichia Pastoris*

The overlapping extension PCR products from example 3 were purified using the Qiaquick kit (Qiagen, Hilden, Germany) in accordance with the manual included. About 0.1 µg of the purified PCR products was cut using the EcoRI restriction endonuclease and cloned via the EcoRI cleavage site into the plasmid vector pGAPZ A (Invitrogen).

Correct orientation of the insert in relation to the promoters was checked with the aid of control cleavages, for example with NcoI.

In each case, a clone with correctly oriented insert was selected, sequenced and preserved.

The corresponding plasmids were named as follows:

Plasmids which contained the known PLE sequence as disclosed in Matsushima et al., (1991) FEBS Lett. 293, 37-41, were called pGAPZ A PLE-ER (the HAEL tetrapeptide was deleted) and pGAPZ A PLE+ER (HAEL tetrapeptide still present).

Plasmids derived from the novel APLE sequence were called pGAPZ A APLE-ER (the HAEL tetrapeptide was deleted) and pGAPZ A APLE-ER (HAEL tetrapeptide still present).

EXAMPLE 5

Constitutive Expression of Pig Liver Esterases in *Pichia Pastoris*

The plasmids pGAPZ A PLE-ER, pGAPZ A PLE+ER, pGAPZ A APLE-ER and pGAPZ A APLE+ER were transformed into *P. pastoris* X-33. The transformation took place in accordance with the instructions of the protocol for the *Pichia* Expressions kit from Invitrogen. The transformants were selected on YPD plates (1% yeast extract, 2% peptone, 2% D-glucose, 2% agar) which contained 100 mg/l zeocin. 52 zeocin-resistant clones were streaked onto YPD plates with 100 mg/l zeocin and preserved in 15% glycerol.

EXAMPLE 6

Qualitative Analysis of the Esterase Activity

*P. pastoris* transformants were cultured on YPD plates with 100 mg/l zeocin at 30° C. for 48 h. The cells were lifted onto Whatman 541 hardened ashless 70 mmØ filters and air-dried. The filters were incubated with a solution of 6 mg of α-naphthyl acetate (Sigma, dissolved in 500 µl of acetone), 2.5 mg of tetrazotized o-dianisidine (Fast Blue Salt BN, Sigma, dissolved in 125 µl of water) and 5 ml of 0.1 M potassium phosphate buffer, pH 7, in order to visualize the esterase activity by a color reaction.

Activities were detected in all transformants which had integrated one of the 4 plasmids pGAPZ A PLE-ER, pGAPZ A PLE+ER, pGAPZ A APLE-ER and pGAPZ A APLE+ER. This proves the expression of functional proteins having esterase activity. As a check, a clone with integrated empty vector was also tested in the same way. In this case, no significant esterase activity was visible in the comparable reaction period.

EXAMPLE 7

Stereoselective Esterase Activity in Relation to methyl 5-chloro-2-(1-methylethyl)-4-pentenoate

*P. pastoris* transformants as described in example 6 were cultured on YPD plates with 100 mg/l zeocin at 30° C. for 48 h. The cells were lifted onto Whatman 541 hardened ashless 70 mmØ filters and air-dried. The filters were incubated either with substrate solution A (100 µl of racemic methyl 5-chloro-2-(1-methylethyl)-4-pentenoate, 200 µl of 0.1 M potassium phosphate buffer, pH 8; 150 µl of 10 mg/ml phenol red; 450 µl of DMSO; 650 µl of $H_2O$) or with substrate solution B (identical to solution A but employing methyl (2S,4E)-5-chloro-2-(1-methylethyl)-4-pentenoate instead of the racemate).

Owing to the specific esterase activity on the substrates, the liberation of acid on hydrolysis of the ester substrate results in a pH decrease which in turn leads to a change in the color of the phenol red indicator to yellow.

It emerged from this that transformants containing the plasmid pGAPZ A APLE-ER gave signals (yellow coloration around the colony) after incubation for 3 to 4 hours if they were tested on substrate solution A, whereas no significant conversion could be found with substrate solution B (FIG. 1).

Transformants obtained with the plasmids pGAPZ A PLE-ER or pGAPZ A PLE+ER showed no reaction with substrate solutions A or B under the same conditions.

This showed that the recombinant rAPLE has a substrate specificity different from recombinant rPLE and that hydrolysis of methyl 5-chloro-2-(1-methylethyl)-4-pentenoate using rAPLE takes place stereoselectively for the (R) enantiomer.

EXAMPLE 8

SDS Polyacrylamide Gel Electrophoresis

10 µl of a 2×SDS sample buffer (125 mM Tris-HCl, pH 6.8; 4% SDS, 20% glycerol, 5% β-mercaptoethanol, 0.05% bromophenol blue) were added to 10 µl of commercially available pig liver esterase or 10 µl of the 60-fold concentrated (Centricon Ultrafiltrations-Spin Columns, from Sartorius) supernatants of the *P. pastoris* cultures (72 h at 100 rpm and 28° C. in 250 ml of YPD medium in 2 l Erlenmeyer flasks with baffles) which contained either the plasmid pGAPZ A APLE-ER or an empty pGAPZ A plasmid (control strain).

Figure 2:
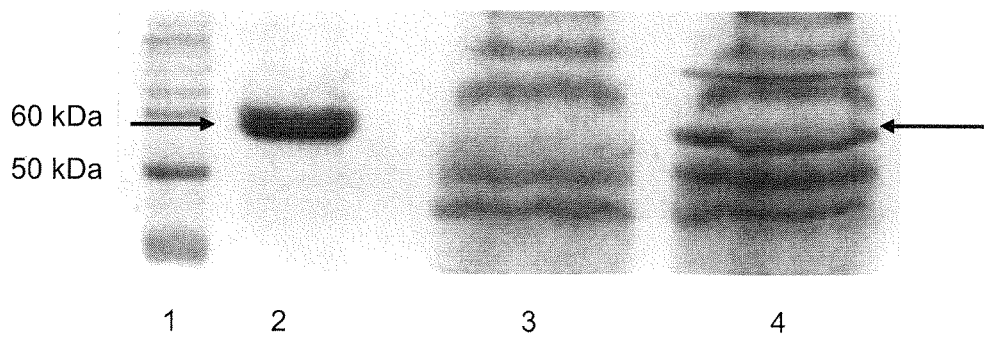
FIG. 2 depicts SDS-PAGE of recombinant APLE.

After the samples had been heated at 95° C. for 5 minutes, the proteins were separated on a 12.5% polyacrylamide gel (4% stacking gel) and stained with Coomassie Brilliant Blue R250 for detection. The SDS-PAGE shows a protein band with the expected size for rAPLE (~60 kDa) in the yeast strain having the pGAPZ A APLE plasmid, but not in the control strain (FIG. 2). The commercially available pig liver esterase which was also analyzed for comparison showed two protein bands in the same size range (arrow in FIG. 2).

EXAMPLE 9

Induced Expression of Pig Liver Esterases with the AOX1 Promoter

The plasmids pGAPZ A PLE-ER, pGAPZ A PLE+ER, pGAPZ A APLE-ER and pGAPZ A APLE+ER were cut with the restriction endonuclease XhoI, and the respective fragments coding for APLE and PLE proteins, with or without ER retention signal, were cloned via the XhoI cleavage site into the pPIC9 vector (Invitrogen). Correct orientation of the fragments in relation to the AOX1 promoter was checked by means of control cuts with the restriction endonuclease NcoI.

The vectors having the AOX1 promoter were named, in analogy to the plasmids named in example 4, pPIC9 PLE-ER, pPIC9 PLE+ER, pPIC9 APLE-ER and pPIC9 APLE+ER, linearized with SalI and transformed into *P. pastoris* KM71. Transformation and selection for His prototrophy took place in accordance with the instructions of the *Pichia* expression kit from Invitrogen. Selected transformants and the KM71 strain were cultured on complete medium in accordance with the *Pichia* expression kit from Invitrogen overnight and induced with 1% methanol for 48 h. The resulting cultures were analyzed by means of the qualitative pH-shift assay described in example 7, testing 2 µl of the cultures in the mixtures in each case. Expression under the control of the inducible AOX1 promoter led to very much higher, by comparison with the situation described for constitutive expression in example 7, rAPLE enzymic activities in relation to racemic methyl 5-chloro-2-(1-methylethyl)-4-pentenoate. The phenyl red color change (red to yellow) was detectable after only a few minutes (FIG. 3). Unexpectedly, the rAPLE activity was independent of the presence of the ER retention signal HAEL at the C terminus, i.e. even cells which expressed rAPLE with ER retention signal showed activity. By contrast, yeast strains for producing rPLE had no activity in relation to racemic methyl 5-chloro-2-(1-methylethyl)-4-pentenoate.

The invention claimed is:

1. An isolated polypeptide having esterase activity and exhibiting an amino acid sequence that is at least 98% identical to the amino acid sequence of SEQ. ID. No. 1.

2. An isolated polypeptide which exhibits at least 98% identity to the amino acid sequence shown in SEQ ID No. 1 and has activity for racemate resolution of 2-alkyl-5-halo-pent-4-enecarboxylic esters of the formula (I)

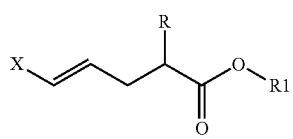

in which R is a C1-C6-alkyl radical, R1 is C1-C4-alkyl and X is chlorine, bromine or iodine.

3. The polypeptide having esterase activity according to claim 1, which exhibits the amino acid sequence modified by a modification selected from the group consisting of mutation, deletion, insertion, extension and fusion.

* * * * *

SEQUENCE LISTING

```
<160> NUMBER OF SEQ ID NOS: 9

<210> SEQ ID NO 1
<211> LENGTH: 548
<212> TYPE: PRT
<213> ORGANISM: Artificial Sequence
<220> FEATURE:
<223> OTHER INFORMATION: rAPLE

<400> SEQUENCE: 1

Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
        35                  40                  45

Ala Pro Pro Gln Pro Ala Glu Pro Trp Ser Phe Val Lys Asn Thr Thr
    50                  55                  60

Ser Tyr Pro Pro Met Cys Cys Gln Glu Pro Ile Gly Gly Gln Met Leu
65                  70                  75                  80

Ser Asp Leu Phe Thr Asn Arg Lys Glu Arg Leu Ile Pro Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Gly Leu Val
        115                 120                 125

Val Gly Gly Ala Ser Thr Tyr Asp Gly Leu Ala Leu Ala Ala His Glu
    130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
            180                 185                 190
```

Gly Asp Pro Gly Ser Val Thr Ile Phe Gly Glu Ser Ala Gly Gly Glu
            195                 200                 205

Ser Val Ser Val Leu Val Leu Ser Pro Leu Ala Lys Asn Leu Phe His
    210                 215                 220

Arg Ala Ile Ser Glu Ser Gly Val Ala Phe Thr Ala Gly Leu Val Arg
225                 230                 235                 240

Lys Asp Met Lys Ala Ala Lys Gln Ile Ala Val Leu Ala Gly Cys
                245                 250                 255

Lys Thr Thr Thr Ser Ala Val Phe Val His Cys Leu Arg Gln Lys Ser
                260                 265                 270

Glu Asp Glu Leu Leu Asp Leu Thr Leu Lys Met Lys Phe Ala Leu
            275                 280                 285

Asp Leu His Gly Asp Pro Arg Glu Ser His Pro Phe Leu Thr Thr Val
            290                 295                 300

Val Asp Gly Val Leu Leu Pro Lys Met Pro Glu Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
            340                 345                 350

Lys Leu Asp Gln Lys Thr Ala Thr Ser Leu Leu Trp Lys Ser Tyr Pro
            355                 360                 365

Ile Ala Asn Ile Pro Glu Glu Leu Thr Pro Val Ala Thr Asp Lys Tyr
            370                 375                 380

Leu Gly Gly Thr Asp Asp Pro Val Lys Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
            420                 425                 430

Arg Pro Ser Phe Ser Ser Asp Lys Lys Pro Lys Thr Val Ile Gly Asp
            435                 440                 445

His Gly Asp Glu Ile Phe Ser Val Phe Gly Phe Pro Leu Leu Lys Gly
            450                 455                 460

Asp Ala Pro Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Glu Gly Tyr Leu Gln Ile Gly Val
            500                 505                 510

Asn Thr Gln Ala Ala Lys Arg Leu Lys Gly Glu Glu Val Ala Phe Trp
            515                 520                 525

Asn Asp Leu Leu Ser Lys Glu Ala Ala Lys Lys Pro Pro Lys Ile Lys
            530                 535                 540

His Ala Glu Leu
545

<210> SEQ ID NO 2
<211> LENGTH: 1647
<212> TYPE: DNA
<213> ORGANISM: Artificial Sequence
<220> FEATURE:
<223> OTHER INFORMATION: rAPLE

<400> SEQUENCE: 2

-continued

| | |
|---|---|
| gggcagccag cctcgccgcc tgttgtggac actgcccagg gccgagtcct ggggaagtac | 60 |
| gtcagcttag aaggcctggc acagccgtg gccgtcttcc tgggagtccc ttttgccaag | 120 |
| cccctctcg gatccttgag gtttgctccg ccgcagcctg cagaaccatg gagcttcgtg | 180 |
| aagaacacca cctcctaccc tcccatgtgc tgccaagagc caattggggg acagatgctc | 240 |
| tcagatctat ttaccaacag aaaggagagg ctcattccgg agttttctga agactgtctc | 300 |
| tacctaaata tttacacccc tgctgacctg acaaagaggg gcagactgcc ggtgatggtg | 360 |
| tggatccacg gaggaggtct ggtggtgggc ggggcttcca cctatgatgg actggccctc | 420 |
| gctgcgcatg aaaacgtggt ggtggtggcc atccagtacc gcctgggcat ctggggattc | 480 |
| ttcagcacag gggacgaaca cagccggggc aactgggtc acttggacca ggtggccgca | 540 |
| ctgcactggg tccaggagaa catcgccaac tttggaggcg acccaggctc tgtgaccatc | 600 |
| tttggagagt cagcaggagg ggaaagtgtc tctgttctgg tgttgtctcc cttggccaag | 660 |
| aacctcttcc accgggccat ctctgagagt ggcgtggcct tcactgctgg cctggtcagg | 720 |
| aaggacatga aggctgcagc taagcaaatt gctgtccttg ctgggtgtaa aaccaccacc | 780 |
| tcggctgtct tgttcactg cctgcgccag aagtcggagg acgagctctt ggacttaacg | 840 |
| ctgaagatga aattttcgc tcttgatttg catggagacc ccagagagag ccatcccttc | 900 |
| ctgaccactg tggtggatgg agtgctgctg cccaagatgc tgaagagat tctggctgaa | 960 |
| aaggatttca acactgtccc ctacatcgtg ggaatcaaca agcaagagtt tggctggctt | 1020 |
| ctgccaacga tgatgggctt ccccctctct gaaggcaagc tggaccagaa gacgccacg | 1080 |
| tcactcctgt ggaagtccta ccccatcgct aacatccctg gaactgac tccagtggcc | 1140 |
| actgacaagt atttggggg gacagacgac cccgtcaaaa agaaagacct gttcctggac | 1200 |
| ttgatggggg atgtggtgtt tggtgtccca tctgtgacgg tggcccgtca acacagagat | 1260 |
| gcaggagccc ccacctacat gtatgagttt cagtatcgcc caagcttctc atcggacaag | 1320 |
| aaacccaaga cggtgatcgg ggaccacggg gatgagatct tctccgtctt tggttttcca | 1380 |
| ctgttaaaag gcgatgcccc agaagaggag gtcagtctca gcaagacggt gatgaaattc | 1440 |
| tgggccaact tgctcgcag tgggaacccc aatggggagg ggctgcccca ttggccgatg | 1500 |
| tacgaccagg aagaagggta ccttcagatc ggcgtcaaca cccaggcagc caagaggctg | 1560 |
| aaaggtgaag agtggccttt ctggaacgat ctcctgtcca aggaggcagc aaagaagcca | 1620 |
| cccaagataa agcatgctga gctgtga | 1647 |

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
cagaattcat ggctatcggg cagccagcct cgc        33

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
ccggaattca gcctcccctt cacagctcag        30

```
<210> SEQ ID NO 5
<211> LENGTH: 43
<212> TYPE: DNA
<213> ORGANISM: Artificial Sequence
<220> FEATURE:
<223> OTHER INFORMATION: primer

<400> SEQUENCE: 5
tcttcgaaga attcacgatg agatttcctt caatttttac tgc            43

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
gaggctggct gcccagcttc agcctctctt ttctcg                    36

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
agagaggctg aagctgggca gccagcctcg ccg                       33

<210> SEQ ID NO 8
<211> LENGTH: 39
<212> TYPE: DNA
<213> ORGANISM: Artificial Sequence
<220> FEATURE:
<223> OTHER INFORMATION: primer

<400> SEQUENCE: 8
atggtaccga attctcacag ctcagcatgc tttatcttg                 39

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9
atggtaccga attctcactt tatcttgggt ggcttctttg                40
```